(12) United States Patent
Graham et al.

(10) Patent No.: US 8,861,061 B1
(45) Date of Patent: Oct. 14, 2014

(54) LENS ASSEMBLIES, INDEXING ASSEMBLIES THEREFOR, AND METHODS OF INDEXING SAME

(71) Applicant: Ocular Instruments, Inc., Bellevue, WA (US)

(72) Inventors: Raymond D. Graham, Renton, WA (US); Mark A. Latina, North Andover, MA (US)

(73) Assignee: Ocular Instruments, Inc., Bellevue, WA (US)

( * ) Notice: Subject to any disclaimer, the term of this patent is extended or adjusted under 35 U.S.C. 154(b) by 0 days.

(21) Appl. No.: 13/830,252

(22) Filed: Mar. 14, 2013

Related U.S. Application Data

(63) Continuation-in-part of application No. 13/230,687, filed on Sep. 12, 2011, now abandoned.

(51) Int. Cl.
*A61B 3/00* (2006.01)
*A61B 3/117* (2006.01)
*A61B 3/125* (2006.01)

(52) U.S. Cl.
CPC .................. *A61B 3/117* (2013.01); *A61B 3/125* (2013.01)
USPC .......................................... 359/219; 359/205

(58) Field of Classification Search
USPC .......... 351/159, 160 R, 160 H, 205, 219, 221, 351/246, 247; 606/4, 6, 18
See application file for complete search history.

(56) References Cited

U.S. PATENT DOCUMENTS

| | | | |
|---|---|---|---|
| 5,841,510 | A | 11/1998 | Roggy |
| 6,183,085 | B1 | 2/2001 | Roggy |
| 7,419,262 | B2 | 9/2008 | Whalen |
| 7,766,480 | B1 | 8/2010 | Graham |
| 2010/0259669 | A1 | 10/2010 | Wood |

FOREIGN PATENT DOCUMENTS

DE        38 31 929 C2     9/1995

OTHER PUBLICATIONS

Huber, C., "Three Ophthalmological Instruments: The Rotating Contact Glass Holder, the Cutying Forceps and the Diamond Cystotome," in J. Draeger and R. Winter (eds.), vol. 18, "New Microsurgical Concepts II: Cornea, Posterior Segment, External Microsurgery," Series: "Developments in Ophthalmology," Karger, Basel, Switzerland, 1989, pp. 102-106.

Huber, C., and K. Saner, "The Rotating Contact Lens Holder," Klinische Monätsblatter für Augenheilkunde 193(7):78-79, Jul. 1988.

*Primary Examiner* — Mahidere Sahle
(74) *Attorney, Agent, or Firm* — Christensen O'Connor Johnson Kindness PLLC

(57) ABSTRACT

A lens assembly generally includes an ophthalmic contact lens, a rotating collar configured for rotation around at least a portion of an outer surface of the lens, and an indexing assembly configured to provide tactile feedback to a user in the form of increased resistance to relative rotation of the lens and the collar at uniformly spaced indexing positions.

12 Claims, 10 Drawing Sheets

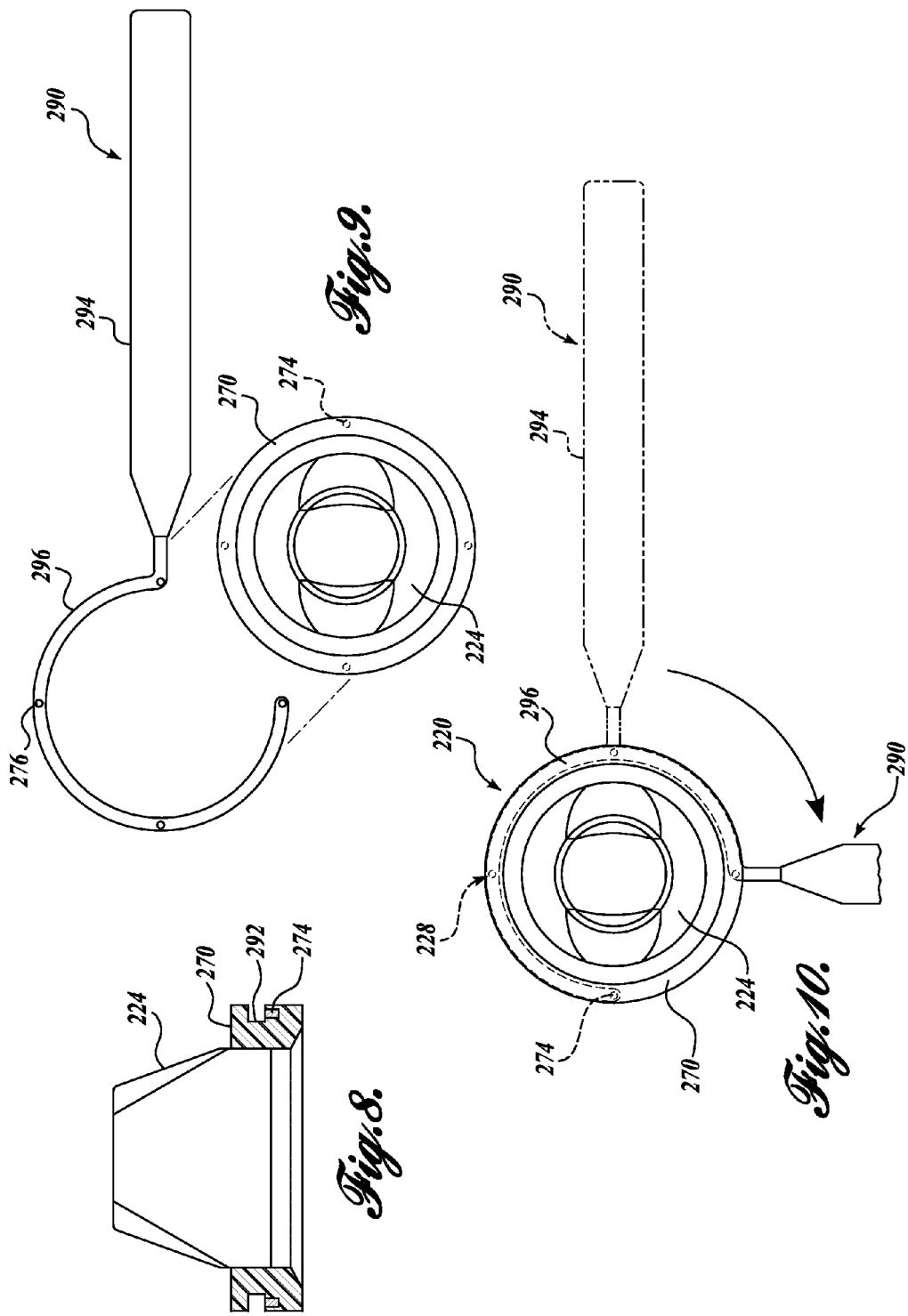

LENS ASSEMBLIES, INDEXING ASSEMBLIES THEREFOR, AND METHODS OF INDEXING SAME

CROSS-REFERENCE TO RELATED APPLICATION

This application is a continuation-in-part of U.S. application Ser. No. 13/230,687, filed Sep. 12, 2011, which is hereby expressly incorporated by reference herein.

BACKGROUND

A lens used in connection with gonioscopy, i.e., the viewing of the periphery of the anterior chamber of the eye, is known as a gonio lens or gonioscope. A gonio lens generally includes a contact lens element and one or more mirrors. The contact lens element has an optical axis and a concave contact surface that conforms to the anterior surface of the cornea of an eye. The contact lens element also has a viewing surface that is offset in an anterior direction from the contact surface. At least one mirror is arranged with its planar surface angled away from the optical axis of the contact lens element in an anterior direction. When the contact lens element is positioned on the eye, the mirrors reflect the light from the periphery of the anterior chamber of the eye into the direction of the observer, typically via a microscope for necessary magnification.

For example, using a gonio lens, the observer can visually assess inflammation or structural defects in the trabecular meshwork and related adjacent structures in the eye. As another example, using a gonio lens that is configured for the dual purposes of viewing and treating an eye, such as an iridotomy goniolaser lens and a trabeculoplasty goniolaser lens (e.g., a Selective Laser Trabeculoplasty lens or SLT lens), the observer may assess the trabecular meshwork before, during, and after the treatment with laser energy to thereby assess the efficacy of the treatment.

As mentioned above, some lenses may include a plurality of mirrors, such as the Ocular Three Mirror Universal, manufactured by Ocular Instruments, Inc., of Bellevue, Wash., wherein the mirrors are circumferentially spaced respectively 120° apart and are mounted at different angles of inclination, such as 59°, 67°, and 73°. Each different mirror angle allows the user to inspect and evaluate different portions of the eye. However, it should be appreciated that some lenses have a plurality of mirrors all having the same angle of inclination, such as the Ocular Posner Diagnostic and Surgical Gonio lens, also manufactured by Ocular Instruments, Inc., which helps reduce the need to rotate the mirror. As another example, the lens may include a single mirror, such as the Ocular Magna View Gonio, also manufactured by Ocular Instruments, Inc.

The selection and position of the specific mirror to be used during an evaluation depends upon the portion of the eye that needs to be evaluated. The selected mirror is generally positioned opposite the area to be evaluated. For example, if the 12 o'clock position of the peripheral retina needs to be evaluated and a mirrored lens is being utilized, an angled mirror can be positioned at the 6 o'clock position of the retina so as to view the affected area.

Whether in a multiple mirror lens or a single mirror lens, it may be necessary to rotate the lens up to 360 degrees to examine the entire retina or other portions of the eye or to conduct a full treatment on the entire eye. Manipulation and positioning of the mirror at the appropriate location relative to the retina is generally accomplished by manually rotating the entire lens device on the eye of the patient until the selected mirror is located in the proper position. This orientation is obtained by rotating the lens between the forefinger and thumb of the user so that the lens is 180° opposite the area to be evaluated. Rotation of the lens can be accomplished with one or two hands depending upon the user.

Devices designed for assisting users with rotation of a contact lens relative to a patient's eye have been developed. For example, U.S. Pat. No. 6,183,085, issued to Roggy et al., is generally directed to an annular peripheral member or jacket for a lens that rotates relative to the lens housing. The rotating jacket includes a projection and groove system that maintains the rotating jacket on the lens housing, but allows for free unfettered rotational movement of the jacket relative to the housing.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a lens assembly is provided. The lens assembly generally includes an ophthalmic contact lens, a rotating collar configured for rotation around at least a portion of an outer surface of the lens, and an indexing assembly configured to achieve precise rotation of the lens relative to the collar in uniform increments, referred to as indexing positions.

In accordance with another embodiment of the present disclosure, an indexing assembly for a lens assembly including a lens is provided. The indexing assembly generally includes a first portion of an indexing assembly associated with an outer surface of the lens, a rotating collar configured for rotation around at least a portion of an outer surface of the lens, and a second portion of an indexing assembly associated with the rotating collar, such that the first and second portions interact to provide one or more indexing positions.

In accordance with another embodiment of the present disclosure, a method of indexing a rotating collar relative to a lens assembly is provided. The method generally includes receiving a rotating collar on an outer surface of a lens assembly, moving the lens assembly relative to the rotating collar, and indexing the rotating collar and the lens assembly at one or more indexing positions.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIGS. 8-10 are respective cross-sectional and top views of a lens assembly in accordance with yet another embodiment of the present disclosure;

DETAILED DESCRIPTION

Figure 1:
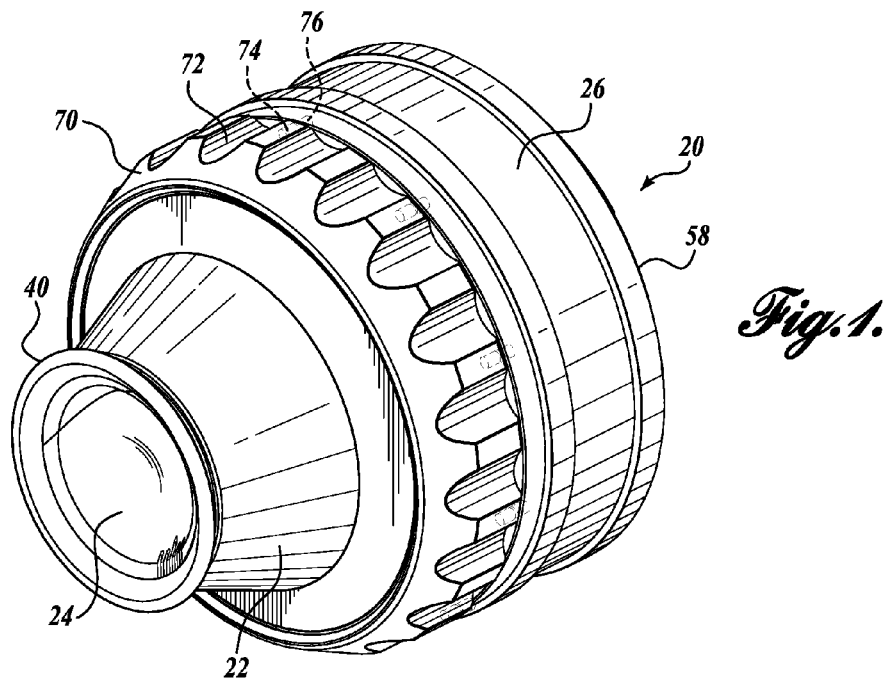
FIGS. 1 and 2 are respective contact end and viewing end isometric views of a lens assembly in accordance with one embodiment of the present disclosure.
Figure 2:
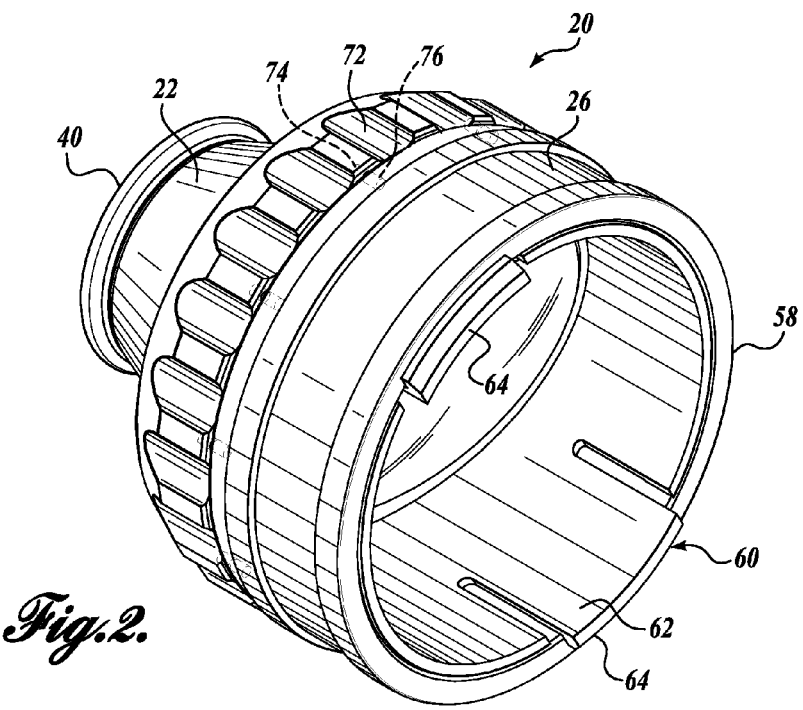

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Accordingly, the following descriptions and illustrations herein should be considered illustrative in nature, and thus, not limiting the scope of the disclosed subject matter.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Embodiments of the present disclosure are generally directed to indexing assemblies and methods of indexing a rotating member relative to a lens assembly, for example, a contact lens assembly used in optometry and ophthalmology. As used herein "indexing" refers to achieving precise rotation of a lens assembly in uniform increments. Each incremental rotated position is sometimes referred to as an "indexing position." At an indexing position, tactile feedback is provided to the user in the form of localized increased resistance to rotary movement from the indexing position. Such resistance may, nevertheless, be manually overcome by a very small movement from one indexing position toward another indexing position. Free rotation is thereafter permitted until an adjacent indexing position is reached.

Referring to FIGS. 1-5, one embodiment of a lens assembly 20 in accordance with the present disclosure can be seen. The lens assembly 20 in the illustrated embodiment includes a housing 22, a lens 24 disposed within the housing 22, and a rotating member 26, shown as a collar, that is configured for indexed rotational movement relative to the housing 22. The rotating member 26 is indexed by an indexing assembly to provide a plurality of indexing positions that help the user orient the positioning of the rotating member 26 relative to the housing 22 and the lens 24.

In the illustrated embodiment, the lens housing 22 is a substantially hollow member including an inner cavity 30 (see FIG. 4), which is designed to receive and protect the lens 24. The lens housing 22 is generally designed and configured to couple with the eye and fit within the eye socket of the patient, to fill the void created by the mirror, and to protect the lens mirror from damage and debris that reduce reflectivity. In that regard, the lens housing 22 of the illustrated embodiment is a housing assembly that includes a first portion 32 and a second portion 34 (see separate first and second portions 32 and 34 in FIGS. 4 and 5), which are configured for mating together to substantially surround and protect the lens 24. At least a portion of the outer surface of the first portion 32 of the housing 22 is frusto-conical in shape so that it can easily be received within the eye socket of the patient.

Although shown in the illustrated embodiment of FIGS. 1-5 as including a housing 22 surrounding the lens 24, it should be appreciated that in other embodiments, the lens assembly need not include a housing or a housing that substantially surrounds the lens. For example, in the illustrated embodiment of FIGS. 6 and 7 (described in greater detail below), the lens assembly 120 does not include a lens housing that fully surrounds the lens 124. Lenses without housings usually include a mirror coating or plating on the outer surfaces of the mirrors, or are made of a material with a high enough refractive index (such as greater than 1.72) that they maintain internal reflectivity regardless of fluid or debris on the lens mirror.

The first portion 32 of the housing 22 of the illustrated embodiment will now be described in greater detail. Referring to FIG. 4, the first portion 32 includes a first end 40 and a second end 42, wherein the diameter of the first end 40 is smaller than the diameter of the second end 42. The first end 40 corresponds with the contact end of the lens 24, i.e., the concave portion of the lens adapted for engagement with a patient's eye (often the cornea). In that regard, the first end 40 of the first portion 32 includes a rim portion 44 defining an opening 46 therethrough (seen in FIG. 3 into the housing cavity 30 within which the lens 24 is mounted. Referring to FIG. 5, from the first end 40 to the second end 42, the inner wall surface 48 of the first portion 32 is substantially frusto-conical in shape to receive a like shaped lens 24. Likewise, the outer wall surface 50 near the first end 40 is also frusto-conical in shape.

Near the second end 42, however, the outer wall surface 52 of the first portion 32 of the housing 22 is substantially cylindrical in shape and designed to mate with the second portion 34 of the housing 22 (see FIG. 5). As can be seen in FIG. 4, the thickness of the outer wall near the second end 42 varies around the circumference of the second end 42, wherein the wall thickness may depend on the type of lens 24 being housed. In addition, the second end 42 is cut along an angled plane to align with the anterior surface of the lens 24. On the outer surface of the first portion 32 of the housing 22, there is an angled shoulder 66 separating the frusto-conical outer wall 50 near the first end 40 and the cylindrical outer wall 52 near the second end 42.

Like the second end 42 of the first portion 32 of the housing 22, the second portion 34 of the housing 22 is also substantially cylindrical in shape. As best seen in FIG. 5, the second portion 34 has an inner diameter that is slightly larger than the other diameter of the second end 42 of the first portion 32. In that regard, the first end 56 of the second portion 34 slips over the second end 42 of the first portion 32 and can be fixedly coupled to the first portion 32. Suitable coupling mechanisms for the first and second portions 32 and 34 of the housing 22 may include, but are not limited to, interference fit, a mating annular protrusion and groove mechanism 54 that can be fit together (see FIG. 5), plastic welding, threading, adhesive, etc. It should further be appreciated that, although illustrated as discreet parts, the first and second portions 32 and 34 of the housing 22 may be integrally formed.

The second end 58 of the second portion 34 is the viewing end of the lens assembly 20 through which the user peers. In general, the viewing end is spaced from the contact end along the line of sight or axis through the lens. At the second end 58, the second portion 34 of the housing 22 also includes a releasable engagement mechanism 60 for releasably engaging the rotating member 26 on the outer surface of the housing 22. In that regard, the engagement mechanism 60 includes one or more moveable tabs 62 that are bendable inward to allow rotating member 26 to slip on and off the housing 22. The tabs 62 act like leaf springs that are normally biased to be in alignment with the cylindrical shape of the second portion 34. From the normal position, the tabs 62 can be bent inwardly by the user to at least a second position. When in the bent second position, the rotating member 26 can be removed from engagement with the second portion 34 of the housing 22.

The tabs 62 each include a protrusion 64 (in the illustrated embodiment, shown as an outward protruding edge) to prevent the rotating member 26 from being removable from the housing 22 when the tabs 62 are in their normal or relaxed positions. Therefore, the tabs 62 allow the rotating member 26 to rotate around the housing 22 without unwanted axial disengagement from the housing 22. In the illustrated embodiment, the engagement mechanism 60 includes two tabs 62. In that regard, two tabs 62 can be simultaneously manipulated by a user using the thumb and index finger. However, it should be appreciated that any number of tabs 62, including one tab or more than two tabs, are within the scope of the present disclosure.

Although shown and described as being removable, it should be appreciated that the rotating member 26 need not be removable from the housing 22. In that regard, the housing 22 may be configured without an engagement mechanism for the rotating member 26. In this example, the rotating member 26 would be permanently rotatably coupled to the housing 22. In another non-limiting example, the rotating member 26 may optionally include a projection and groove system to maintain the rotating member on the housing, as described in U.S. Pat. No. 6,183,085, issued to Roggy et al, the disclosure of which is hereby expressly incorporated by reference.

As mentioned above, the lens 24 is substantially frustoconical in shape and designed to be received within the substantially frustoconical inner cavity 30 of the housing 22. The lens 24 may be held in place, for example, by interference fit, etc. One non-limiting example of a suitable lens is shown and described in U.S. Pat. No. 7,766,480, issued to Graham et al., the disclosure of which is hereby expressly incorporated by reference. As can be seen in FIG. 5, the lens 24 protrudes from the opening 46 in the housing 22 to enable direct contact of the lens 24 with the eye of a patient.

In the illustrated embodiment, the lens assembly 20 has a single mirror 53 positioned at 62° (see FIG. 5); for example, the lens may be an Ocular Magna View Gonio, manufactured by Ocular Instruments, Inc. As mentioned above, other non-limiting examples of lens assemblies may include multiple mirror arrangements, such as the Ocular Three Mirror Universal, wherein the mirrors are circumferentially spaced respectively 120° apart and are mounted at different angles of inclination, for example, 59°, 67°, and 73° relative to the vertical, and the Ocular Posner Diagnostic and Surgical Gonioprism, having a plurality of mirrors all having the same angle of inclination, both also manufactured by Ocular Instruments, Inc.

Figure 3:
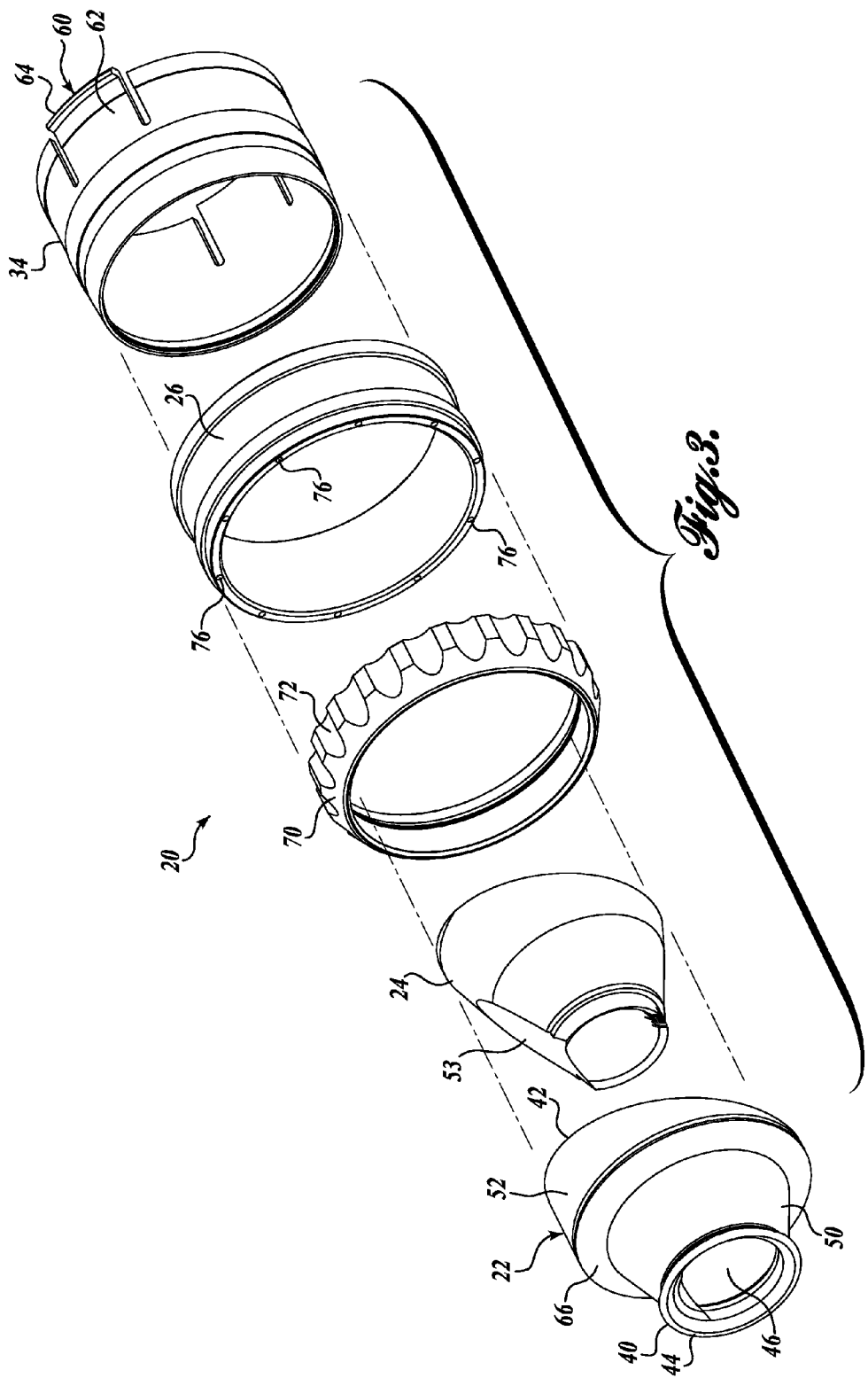
FIGS. 3 and 4 are respective contact end and viewing end exploded views of the lens assembly of FIGS. 1 and 2.
Figure 4:
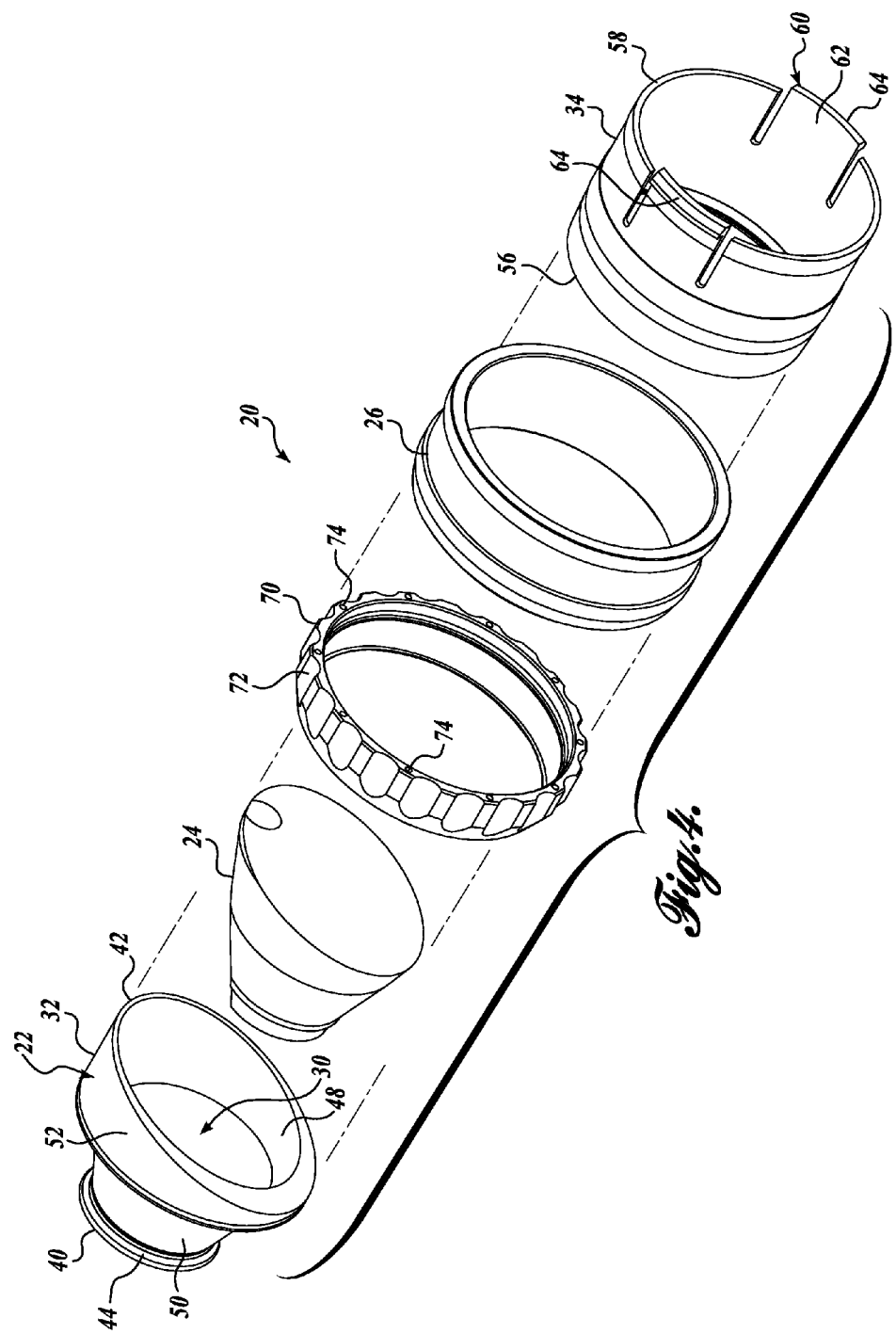
Figure 5:
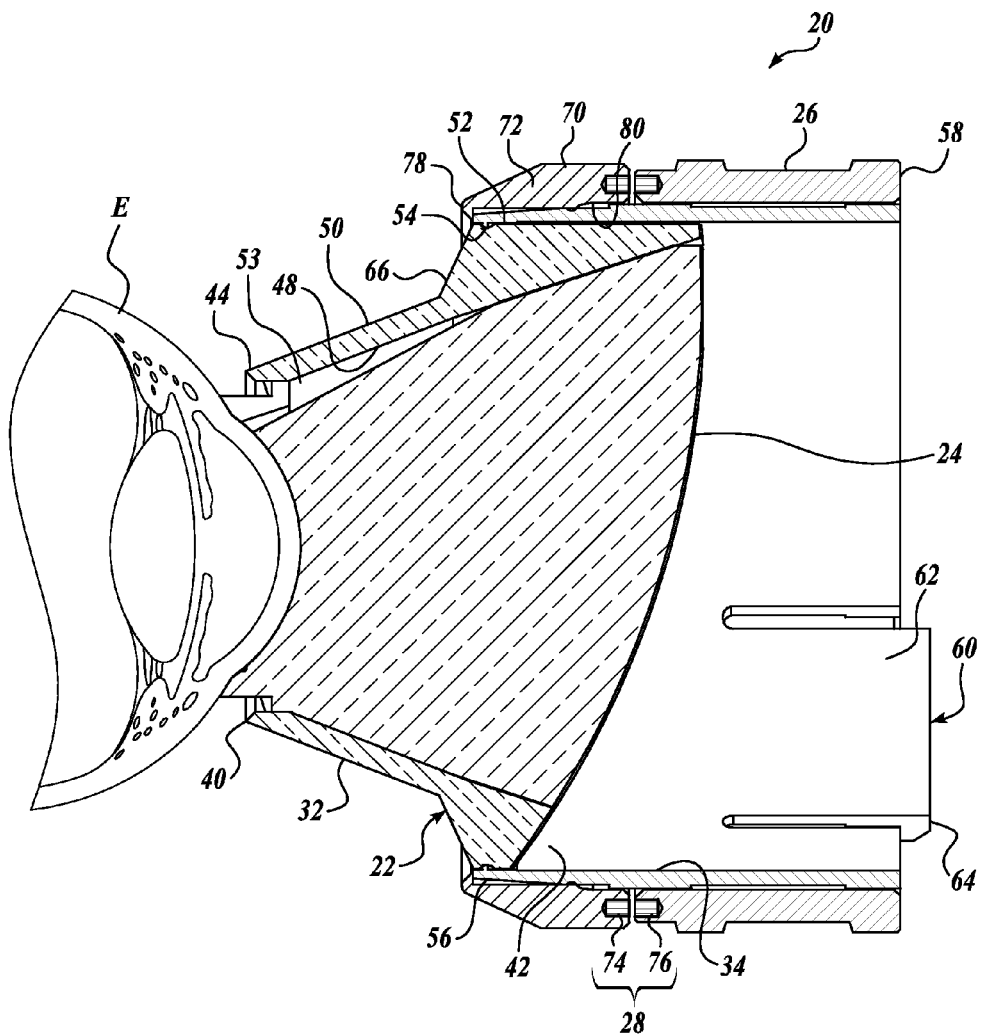
FIG. 5 is a cross-sectional view of the lens assembly of FIGS. 1 and 2.

Referring to FIGS. 3-5, a fixed member 70 is disposed on the outer surface of the second portion 34 of the housing 22 in coaxial position with the rotating member or collar 26. In the illustrated embodiment, the fixed member 70 is an annular collar positioned near the overlapping areas of the first and second portions 32 and 34 of the housing 22. The fixed member 70 has a thickness that extends outwardly from the outer surface of the second portion 34 to provide a gripping surface that enables the user to grip the lens assembly 20 with ease. The common axis of the fixed member 70 and the rotating member 26 intersects the contact surface of the lens.

The fixed member 70 is rigidly attached to the housing 22. In the illustrated embodiment, the mechanism for rigid attachment includes an extending lip 78 for engaging with the first end 56 of the second portions 34 of the housing 22 and mating protrusion and groove mechanism 80 that can be fit together (see FIG. 5). It should be appreciated, however, that other rigid attachment mechanisms, such as interference fit, plastic welding, threading, adhesive, etc., are within the scope of the present disclosure. Moreover, it should be appreciated that the fixed member 70 need not be a discrete part member and may instead be integrally formed with or an integral part of the housing 22.

In the illustrated embodiment, the fixed member 70 is an annular collar having rounded grooves 72 to help the user grip the lens assembly 20. However, the fixed member 70 need not be a collar, and instead may be one or more grooves for positioning the user's finger used to manipulate the lens assembly 20 when adjusting the lens assembly relative to the patient's eye. Referring to FIG. 5, a first portion 74 of an indexing assembly 28 is disposed in the thickness of the fixed member 70 between knurled grooves 72, which will be described in greater detail below.

Adjacent the fixed member 70 disposed on the outer surface of the second portion 34 of the housing 22 near the second end 58 of the second portion 34 (or the viewing end) of the lens assembly 20 is the rotating member 26. The rotating member 26 is configured to rotate relative to the fixed member 70 and the housing 22. In that regard, the rotating member 26 is an annular collar having a thickness, such that the rotating member 26 extends outwardly from the outer surface of the second portion 34 of the housing 22. Referring to FIGS. 3 and 5, a second portion 76 of the indexing assembly 28 is disposed in the thickness of the rotating member 26, which is used together with the first portion 74 of the indexing assembly 28, as described in greater detail below.

It should be appreciated that the fixed and rotating magnetic members 74 and 76 are designed for magnetically coupling with one another and may be one of either magnets or materials capable of having a magnetic attraction with a magnet. The magnetic members 74 and 76 may be disposed in the respective fixed member 70 and rotating member 26 by being integrally formed with the fixed member 70 and rotating member 26, welded, threaded, or adhered thereto, fit into holes by an interference fit, etc.

Movement of the housing 22 (and therefore the lens 24) relative to the rotating member 26 will now be described in detail. As mentioned above, the lens assembly 20 is configured to contact the eye E of the patient and to rotate on the eye E (see FIG. 5), so as to properly align and orient the appropriate mirror at the appropriate location opposite the area of the retina or other eye portion to be evaluated or treated. To move the lens assembly 20, the user holds the rotating member 26 stationary, for example, by gripping the rotating member 26 between his thumb and index finger. Because the rotating member 26 rotates freely relative to the rest of the lens assembly 20, the user then uses his middle finger to rotate the rest of the lens assembly 20, thereby rotating the lens 20 on the eye E of the patient. In the illustrated embodiment of FIGS. 1-5, the user rotates the lens assembly 20 with his middle finger gripping one of the knurled grooves 72 on the fixed member 70. Using this method, rotation of the lens 20 on the eye of the patient can be accomplished by the user with one hand.

Because the user holds the rotating member 26 stationary, the user has improved rotation technique over previous lenses that did not include rotating members 26. Such improved rotation technique decreases the chance that the lens 24 will disengage from (or "pop off") the eye of the patient. Also, improved rotation technique reduces the formation of air bubbles in the fluid between the lens and the eye, which can reflect light and affect the user's ability to evaluate and/or treat the patient's eye.

As mentioned above, the rotating member 26 is indexed by an indexing assembly 28 which is configured to provide increased resistance to rotary movement of the rotating collar 26 when it is in any one of uniformly spaced indexing positions relative to the housing 22 and the lens 24. In the illustrated embodiment of FIG. 1-5, the indexing assembly 28 is a magnetic system having first and second portions 74 and 76, shown as a plurality of rotating and fixed magnetic members disposed in respective rotating and fixed members 26 and 70.

Although shown and described as rotating and fixed magnetic members being disposed in respective rotating and fixed members 26 and 70, it should be appreciated that the first and second portions of the indexing assembly 28 can be associated with the respective fixed and rotating members 70 and 26 and need not be disposed within. As non-limiting examples, the rotating and fixed magnetic members may be positioned on any outer or inner surface of the respective rotating and fixed members 26 and 70. Moreover, the fixed magnetic members 74 may be associated with an outer surface of the lens 24 or an outer surface of the housing 22, and need not be associated with a discrete fixed member 70.

In the illustrated embodiment, the first portion 74 of the indexing assembly 28, shown as a plurality of fixed and uniformly spaced magnetic members, and the second portion 76 of the indexing assembly 28, shown as rotating magnetic members, magnetically engage with one another to provide rotation resistance that can be overcome by the user, but that indicates a certain rotation position to the user. For example, in the illustrated embodiment, the fixed member 70 and the rotating member 26 each include ten magnetic members. As the user rotates the lens assembly 20 around the eye of the patient, he encounters ten resistance points providing tactile feedback that an indexing position has been reached, each spaced about 36° from each other. The user can, therefore, easily count to ten to know that a 360° rotation has been completed.

Although shown and described as a magnetic indexing assembly, which is preferred, it should be appreciated that other indexing assemblies 28 are also within the scope of the present disclosure. Suitable indexing assemblies 28 may include, but are not limited to, stopping systems using spring-detents, coils with balls or cantilevers, plungers for positive rotation stops, etc. As mentioned above, these alternative indexing assemblies could be integrated into anterior retaining rings, as outer diameter features, as discreet collars, etc.

Instead of counting to ten, one or more of the rotating member 26, the housing 22, and the fixed member 70 may include visual marks on their external surfaces to indicate the beginning or zero position of the 360° rotation, as well as subsequent numbered points. For example, suitable markings may be 0, 1, 2, 3, 4, 5, 6, 7, 8, 9, at which point the user returns to zero. Moreover, visual marks may be included on the lens 24. Although the marks would not be in focus when the user is examining or treating the ocular anatomy, the marks will define useful start and end points for the user.

The inventors discovered the need for an indexing assembly when they began conducting procedures using sub-threshold lasers. In some procedures using lasers, laser lesions are not sub-threshold, and, therefore, the laser lesions are visible to the user conducting the procedure. However, in sub-threshold laser procedures, such as selective laser trabeculoplasty (SLT), a treatment to improve eye fluid drainage in glaucoma patients, laser lesions may not be visible to the user conducting the procedure. In an SLT procedure, laser spots are placed adjacent each other in a series, then the lens is rotated a certain angle of rotation and another series of laser spots are placed, until 360° of the patient's eye have been treated. Having no guiding lesions in this kind of procedure, it is easy for a user to misjudge full rotation around the eye, by either falling short and not treating the entire eye or overlapping treatment in portions of the eye. The indexing assembly 28 described herein therefore improves the user's ability to perform these procedures because it allows the user to count a certain number of indexing positions or to return to an indexing zero position to know that a 360° rotation around the eye has been completed.

In another application of embodiments of the present disclosure, a plurality of indexing marks can be used for relative measurements of ocular structures. For example, if the indexing assembly 28 is configured to index every 10° and is used on a lens that has an embedded indicator, as described in U.S. Pat. No. 7,766,480, issued to Graham et al., the disclosure of which is hereby expressly incorporated by reference, the user would be able to estimate the angular size of ocular structures.

Moreover, in ocular lenses for which there are a plurality of mirrors, for example, four different mirrors in a square of diamond pattern, the indexing assembly 28 can be configured to index at four 90° angles locations to index with each of the different mirrors. Such indexing in this type of lens will save the user time in accurately rotating the lens to correspond with the desired mirror.

The magnetic members shown in the illustrated embodiment are 0.75 mm diameter cylindrical magnetic members. However, it should be appreciated that other sizes of magnetic members are also within the scope of the present disclosure. One advantage of using smaller diameter magnetic members is that the outer diameter of the rotating member 26 and the fixed member 70 can be minimized, thereby reducing the overall diameter of the lens assembly 20. Reducing the overall diameter of the lens assembly 20 allows for the lens assembly 20 to be used with all patients, even those having deep set eyes.

Although shown in the illustrated embodiment as using ten magnetic members, it should be appreciated that any number of indexing magnetic member pairs may be used in the indexing assembly 28, for example, 3, 4, 8, 9, 12, 15, 18, 20, 24, or 36. Moreover, the matching of magnetic members on the rotating member 26 and the fixed member 70 need not be equal. However, a certain number of matching magnetic members are required to provide adequate indexing resistance for the user. For example, the inventors found that moving one magnetic member on either of the rotating member 26 and the fixed member 70 relative to ten indexing magnetic members on the other of the rotating member 26 or the fixed member 70 did not provide adequate indexing resistance. Not wishing to be bound by theory, the inventors hypothesize that a magnetic member matching of two or more, such as ratios of 2:10, 4:10, 5:10, 6:10, and 8:10 may also provide adequate indexing resistance.

Another advantage of a magnetic indexing assembly 28 is that there are no moving parts in the indexing assembly 28, which simplifies cleaning of the lens assembly 20. Moreover, in the illustrated embodiment, the lens assembly 20 can be easily dismantled for cleaning after individual use. To disengage the rotating member 26 from the housing 22, the user simply presses tabs 62 inward with his thumb and index or fore finger and slips the rotating member 26 over the protruding edges 64 of the tabs 62 and off the housing 22. However, it should be appreciated that non-removable rotating members are within the scope of the present disclosure and may have a reduced overall lens assembly diameter than lens assemblies having removable rotating members.

Turning now to FIGS. 6-10, lens assemblies 120 and 220 designed and configured in accordance with other aspects of the present disclosure are shown. It should be appreciated that the various embodiments shown in FIGS. 6-10 are substantially similar to the lens assembly 20 shown in FIGS. 1-5, except primarily for differences regarding, respectively, the housing and the rotating member. Like numerals for the embodiment shown in FIGS. 1-5 are used for the alternate embodiments shown in FIGS. 6-10, except in the 100 and 200 series.

Figure 6:
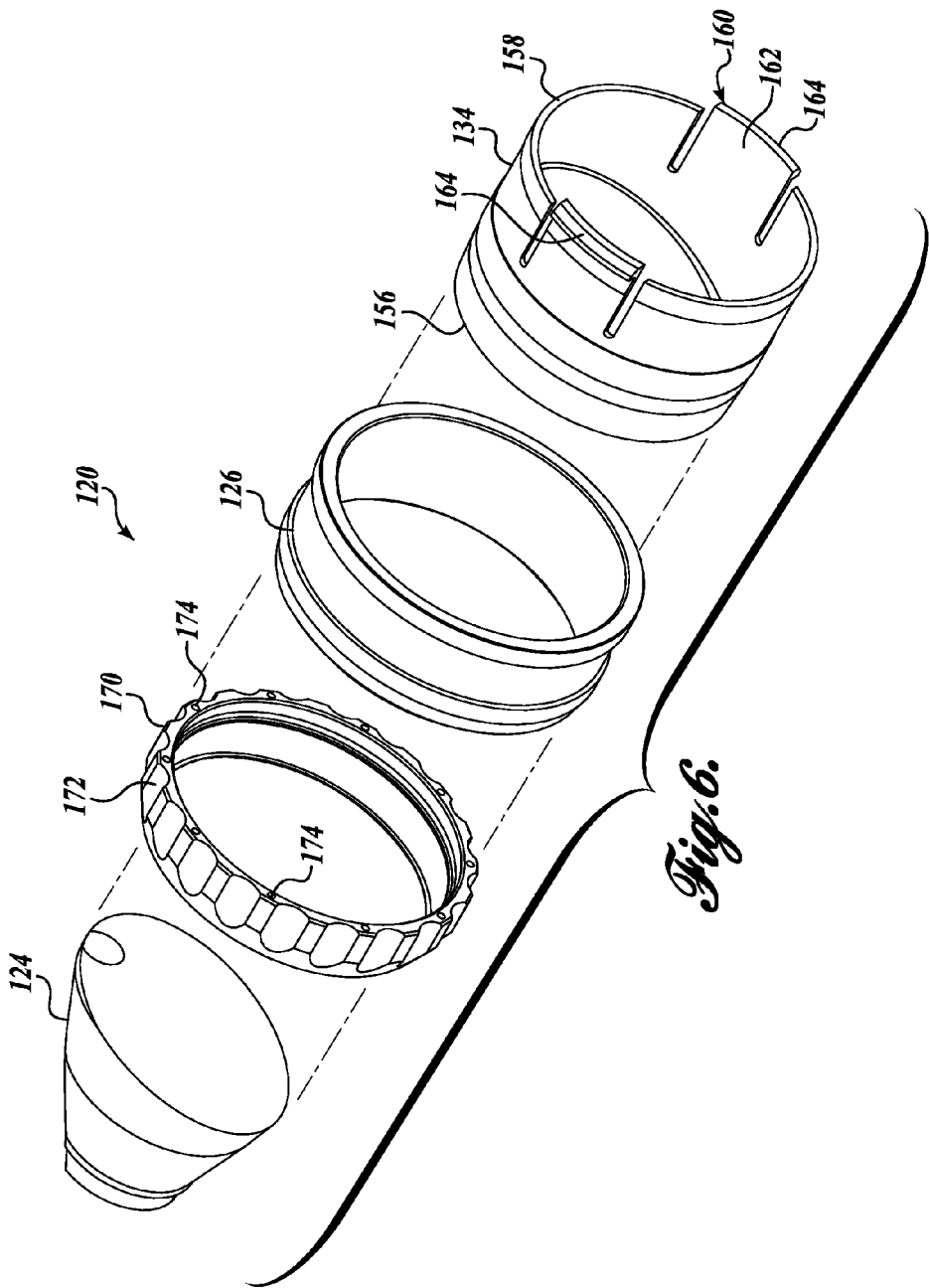
FIGS. 6 and 7 are respective exploded and cross-sectional views of a lens assembly in accordance with another embodiment of the present disclosure.
Figure 7:
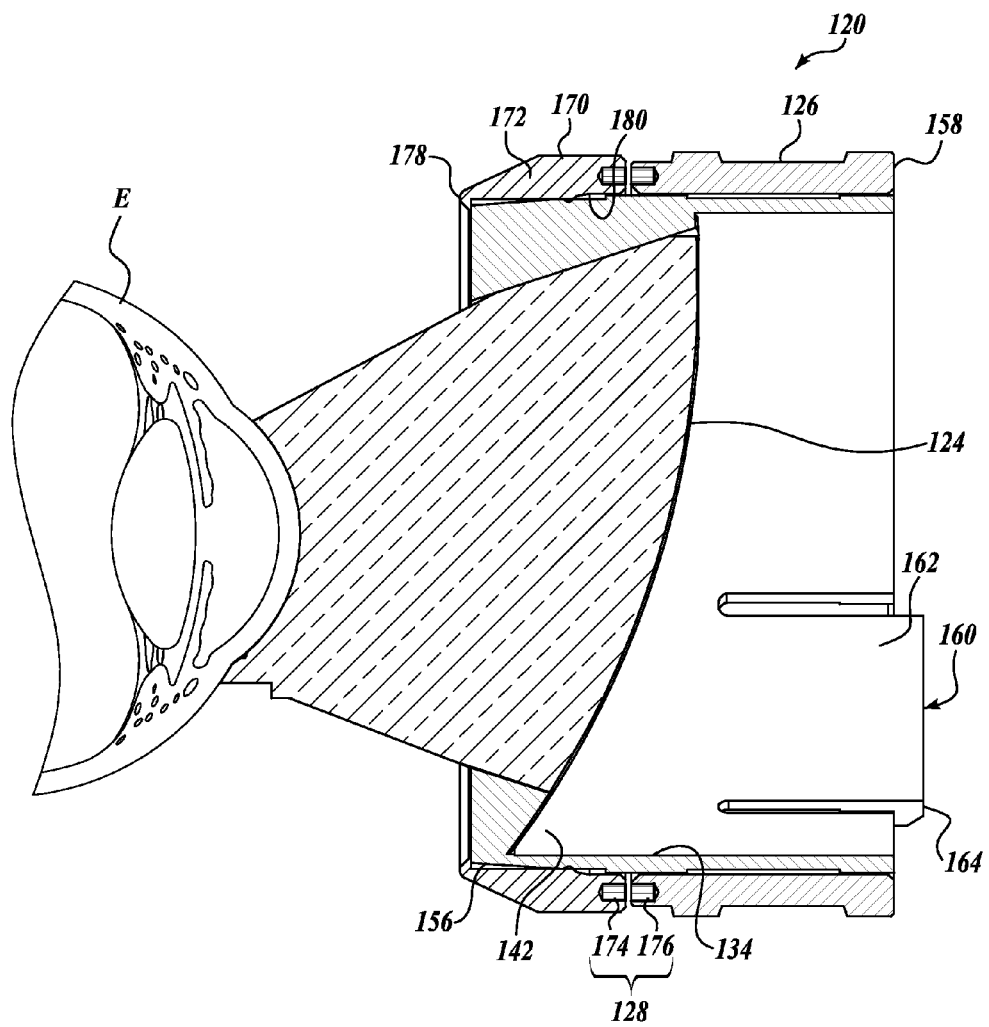

Referring first to the illustrated embodiment in FIGS. 6 and 7, the lens assembly 120 includes an ophthalmic contact lens 124 that is not fully housed in a housing. In that regard, the lens 124 is substantially unhoused. As mentioned above, lenses without housings usually include a mirror coating or plating on the outer surfaces of the mirrors, or are made of a material with a high enough refractive index (such as greater than 1.72) that they maintain internal reflectivity regardless of fluid or debris on the lens mirror. As seen in FIG. 7, the lens 124 is supported by partial housing portion 134, upon which fixed member 170 and rotating member 126 are mounted.

Referring now to the illustrated embodiment in FIGS. 8-10, the lens assembly 220 has a rotatable handle assembly 290 that is configured to be held by the user. In that regard, the lens assembly includes an ophthalmic contact lens 224 and a fixed member 270 having an annular groove 292. The handle assembly 290 includes a handle 294 and a lens coupling member 296, wherein the lens coupling member 296 is configured to be received within the annular groove 292 of fixed member 270.

The lens coupling member 296 of the handle assembly 290 is a rotatable member, capable of indexing at a plurality of positions. In that regard, the lens coupling member 296 includes an indexing assembly 228. In the illustrated embodiment, the indexing assembly 228 includes a plurality of magnetic members 276 associated with the lens coupling member 296 that are configured to interface with magnetic members 274 associated with the annular groove 292 of the fixed member 270. Although illustrated and described as a magnetic indexing assembly, which is preferred, it should be appreciated that other indexing assemblies may also be used with this embodiment, including, but not limited to, stopping systems using spring-detents, coils with balls or cantilevers, plungers for positive rotation stops, etc.

The handle orientation can therefore be rotated to a plurality of indexing positions so as to provide optimal handle location for the user. Such indexing may be particularly useful when the user is using a lens 224 having a plurality of different mirrors, or also for switching between right and left hand use.

Figure 11:
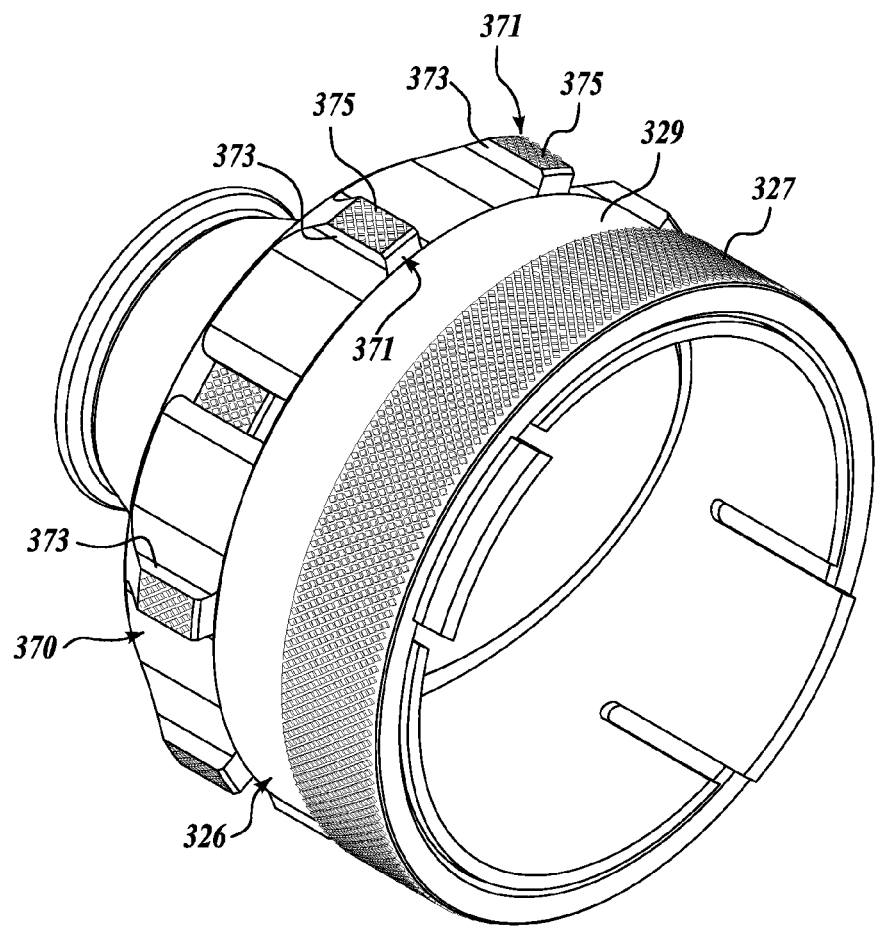
FIG. 11 is a viewing end perspective of another modified lens assembly in accordance with the present invention.
Figure 12:
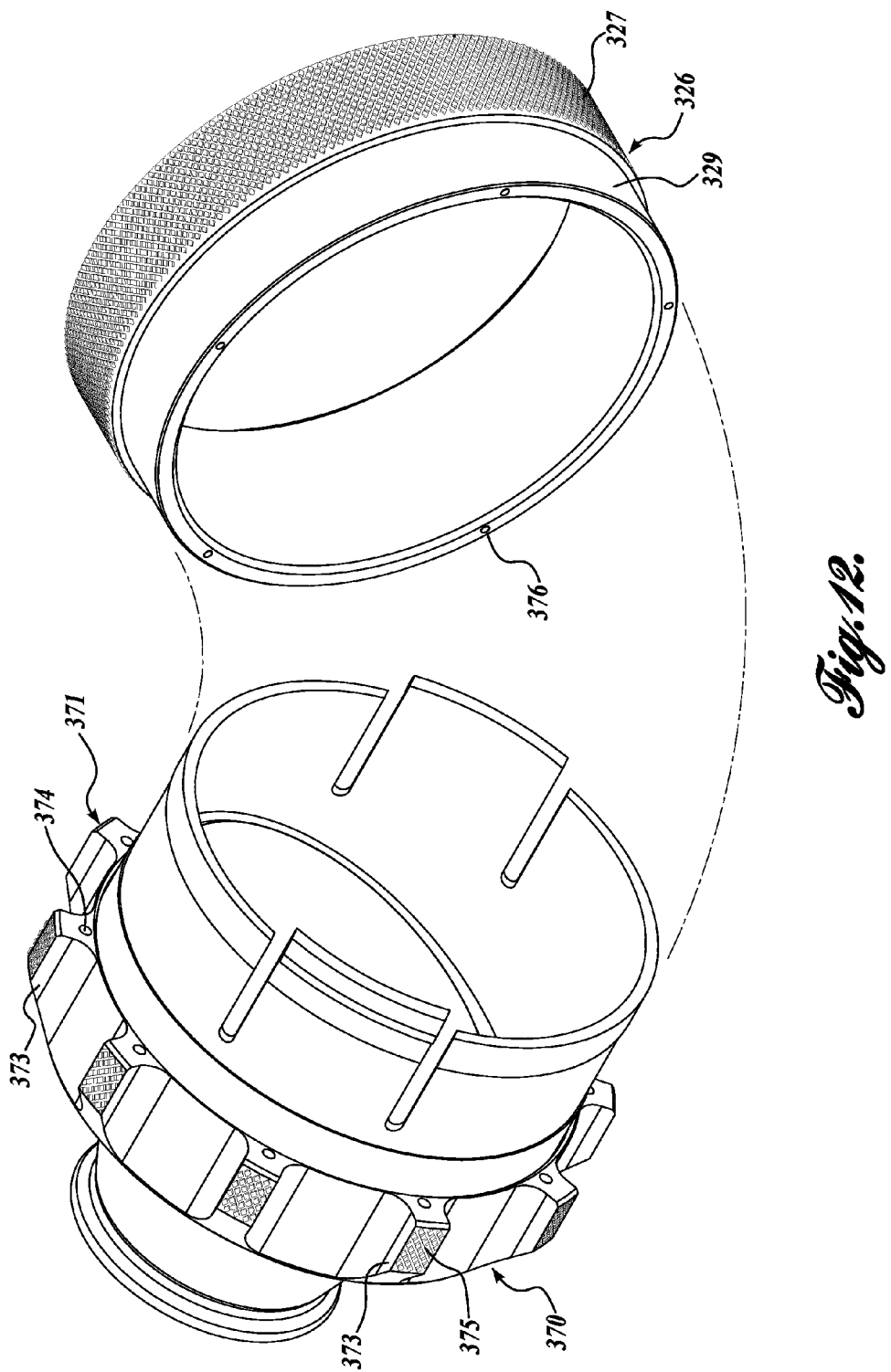
FIG. 12 is a corresponding perspective with some parts shown in exploded relationship.
Figure 13:
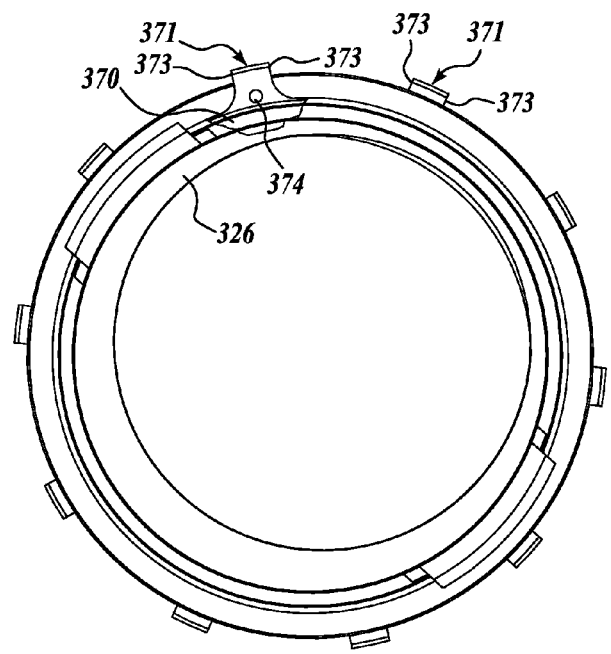
FIG. 13 is a viewing end elevation thereof with the parts assembled and some parts broken away.

The additional embodiment of the present invention shown in FIGS. 11-13 is very similar to the embodiment described above with reference to FIGS. 1-5. The primary differences are features of the exterior of the rotating member 326 (which corresponds to the rotating member 26 of the embodiment of FIGS. 1-5); exterior features of the fixed member 370 (which corresponds to the fixed member 70 of the embodiment of FIGS. 1-5); and the modified magnetic indexing assembly described below.

Concerning the modified rotating member 326, on its cylindrical outer surface a marginal section 327 toward the edge remote from the fixed member has diamond pattern knurling. The rotatable member has a smooth cylindrical section 329 in the marginal portion closest to the fixed member 370. The knurled section provides a convenient and secure gripping surface along the area most remote from the fixed member 370 so that more room is provided for the finger used to rotate the lens by movement of the fixed member. For example, part of the fingertip may engage the smooth section 329 and slide along it without catching or otherwise interfering with rotation of the fixed member 370.

Concerning the fixed member 370, radial ribs 371 are provided at uniform circumferentially spaced locations, corresponding to the uniform increments of indexing rotation. Whereas the grooves of the fixed member described with reference to FIGS. 1-5 are rounded and closely spaced together, providing the ribs 371 at more widely spaced locations results in a much wider depression between adjacent ribs for receiving the pad of a fingertip used to actuate the rotary motion. Preferably the distance between adjacent ribs (measured in a circumferential direction at the midpoint of the height of the ribs) is at least twice the width of a rib (also measured at the midpoint of the height). Also, the ribs have radial leading and trailing surfaces 373 terminating at sharp outer corners, and diamond knurling along the narrow, radially outer faces 375. Further, the radial ribs project significantly beyond the outermost surface of the adjacent part of the rotating member 326. In combination, the wider depressions between radial ribs, radial surfaces projecting beyond the rotating member, sharp outer corners, and the knurled tops combine to enhance the fit of the operative finger used for rotating the lens, i.e., there is significantly less chance that the finger either will not catch on a rib when desired or will slip off during attempted rotation.

With respect to the magnetic indexing components, as seen in FIG. 12, one small cylindrical bar magnet 374 (0.75 mm in diameter and 1 mm long in a representative embodiment) is secured in a blind bore at the base or root portion of each rib. In this embodiment, ten such ribs are provided, spaced 36 degrees apart, and the increment of indexing movement is correspondingly 36 degrees. There is direct visualization of the amount of the increment of rotation and the spacing of the ribs. The filleted root portions of the ribs also provide a convenient and sturdy location for the blind bores in which the magnets 374 are secured. The outer faces of the magnets are preferably precisely flush with the faces of the ribs adjacent to the rotating ring 326. On the rotatable ring, identical magnets 376 are provided at five uniformly spaced locations, i.e., 72 degrees apart. The exposed faces of magnets 376 also are precisely flush with the annular face of the rotating member which is closest to the fixed member 370 when the parts are assembled. As used herein, "precisely flush" means no part of the magnet extends beyond the face in which it is secured, and any indentation of the magnet is less than 0.1 mm. This arrangement of the magnets has been found to achieve the desired indexing rotation of the two members 326, 370 relative to each other. Although the magnets are arranged with opposite poles facing each other, the magnetic attraction is essentially nil until magnets of the rotating member are aligned with magnets of the fixed member. A definite "clicking" action is felt as the magnets align, but even an extremely small rotation from the aligned position essentially eliminates any perceptible magnetic attraction to an indexing position. For example, movement of 0.75 mm from an indexing position results in no alignment of adjacent magnets and no noticeable attraction that could interfere with rotation between indexing positions. The user can see the indexing increment due to the magnets being located in each of the ribs, and receives the desired tactile feedback based on the highly localized magnetic attraction achieved when an indexing position is reached, which increases the resistance to rotation at the indexing position.

In the end view of FIG. 13, the ribs 371 can be seen with their radial leading and trailing surfaces 373 projecting beyond the rotating member. At one location toward the top, the rotating member is broken away so that the entire rib is revealed, including the magnet 374 secured in a blind bore at its base or root portion.

Figure 14:
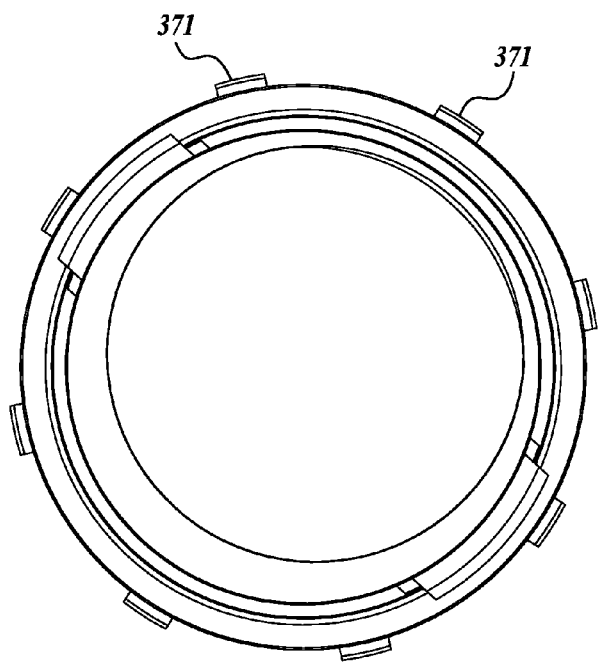
FIG. 14 is an end elevation corresponding to FIG. 13 showing an additional modification for a lens assembly in accordance with the present invention.

In the modification of FIG. 14, eight equally spaced ribs 371 are provided on the fixed member, spaced 45 degrees apart. Each of the eight ribs has a magnet secured in its root portion, the same as the magnets for the ten rib embodiment of FIGS. 11-13. Four uniformly spaced magnets are provided on the rotating member, spaced 90 degrees apart, which results in a balanced attraction for eight 45 degree increments of movement (indexing positions) to achieve a total of 360 degrees or one full rotation.

While illustrative embodiments have been illustrated and described, it will be appreciated that various changes can be made therein without departing from the spirit and scope of the disclosure. For example, while the invention has sometimes been described with respect to a Gonio lens, the invention applies to any ophthalmic contact lens for which rotation of the lens contact end on the eye is necessary or desirable.

The embodiments of the disclosure in which an exclusive property or privilege is claimed are defined as follows:

1. A lens assembly, comprising:
   (a) an ophthalmic contact lens having a contact end and a viewing end;
   (b) a rotating collar configured for rotation around at least a portion of an outer surface of the lens; and
   (c) an indexing assembly constructed and arranged to provide tactile feedback to a user in the form of increased resistance to relative rotation of the lens and the collar at uniformly spaced indexing positions that correspond to a plurality of relative angular positions of the lens and the collar, said increased resistance to relative rotation of the lens and the collar being selected to be manually overcome by the user by a small relative rotary movement of the lens and the collar from an indexing position toward another indexing position enabling free rotation movement until another indexing position is reached.

2. The lens assembly of claim 1, wherein at least a first portion of the indexing assembly is associated with the rotating collar.

3. The lens assembly of claim 2, the lens including a lens housing in which the lens is mounted, and wherein at least a second portion of the indexing assembly is associated with the lens housing.

4. The lens assembly of claim 3, wherein the lens housing further includes a fixed collar adjacent an outer surface of the lens.

5. The lens assembly of claim 4, wherein at least a portion of the indexing assembly is associated with the fixed collar.

6. The lens assembly of claim 3, wherein the indexing assembly is a magnetic assembly.

7. The lens assembly of claim 3, wherein one of the first and second portions of the indexing assembly includes one or more magnets.

8. The lens assembly of claim 7, wherein the other of the first and second portions of the indexing assembly includes one or more substrates configured for attraction with the one or more magnets.

9. An indexing assembly for a lens assembly including an ophthalmic contact lens, the indexing assembly comprising:
   (a) a first portion of an indexing assembly associated with an outer surface of the lens;
   (b) a rotating collar configured for rotation around at least a portion of an outer surface of the lens; and
   (c) a second portion of an indexing assembly associated with the rotating collar, such that the first and second portions interact to provide tactile feedback to a user in the form of increased resistance to relative rotation of the lens and the collar at uniformly spaced indexing positions, said increased resistance to relative rotation of the lens and the collar being selected to be manually overcome by the user by a small relative rotary movement of the lens and the collar from an indexing position toward another indexing position enabling free movement therefrom until another indexing position is reached.

10. The assembly of claim 9, wherein at least one of the first portion and collar of the indexing assembly includes one or more magnets.

11. The assembly of claim 10, wherein the other of the first portion and collar of the indexing assembly has one or more substrates configured for attraction with the one or more magnets.

12. A method of indexing a rotating collar relative to a lens assembly having an ophthalmic contact lens, which method comprises:
   (a) receiving a rotating collar on an outer surface of a lens assembly having an ophthalmic contact lens;
   (b) manually moving the lens assembly relative to the rotating collar; and
   (c) indexing the rotating collar and the lens assembly by providing tactile feedback to a user in the form of increased resistance to relative rotation of the lens assembly and the collar at uniformly spaced indexing positions, said increased resistance to relative rotation of the lens assembly and the collar being selected to be manually overcome by the user by a small relative rotary movement of the lens assembly and the collar from an indexing position toward another indexing position enabling free movement therefrom until another indexing position is reached.

* * * * *